US012778541B2

(12) United States Patent
Dhatt et al.

(10) Patent No.: US 12,778,541 B2
(45) Date of Patent: Nov. 3, 2026

(54) ANATOMY-DIRECTED ULTRASOUND

(71) Applicant: FUJIFILM SonoSite, Inc., Bothell, WA (US)

(72) Inventors: Davin Dhatt, Woodinville, WA (US); Paul Danset, Kirkland, WA (US); Thomas Duffy, Stanwood, WA (US); Christopher White, Vancouver (CA); Andrew Lundberg, Woodinville, WA (US)

(73) Assignee: FUJIFILM SonoSite, Inc., Bothell, WA (US)

( * ) Notice: Subject to any disclaimer, the term of this patent is extended or adjusted under 35 U.S.C. 154(b) by 0 days.

(21) Appl. No.: 19/343,574

(22) Filed: Sep. 29, 2025

(65) Prior Publication Data

US 2026/0020839 A1 Jan. 22, 2026

Related U.S. Application Data

(62) Division of application No. 18/182,196, filed on Mar. 10, 2023, now abandoned.

(51) Int. Cl.
*A61B 8/00* (2006.01)
*A61B 8/08* (2006.01)
*G06N 3/045* (2023.01)

(52) U.S. Cl.
CPC .............. *A61B 8/085* (2013.01); *A61B 8/463* (2013.01); *A61B 8/469* (2013.01); *A61B 8/5207* (2013.01); *G06N 3/045* (2023.01)

(58) Field of Classification Search
CPC ...................................................... A61B 8/085
See application file for complete search history.

(56) References Cited

U.S. PATENT DOCUMENTS

| | | | |
|---|---|---|---|
| 8,956,296 | B2 | 2/2015 | Lundberg et al. |
| 2015/0213613 | A1 | 7/2015 | Prevost et al. |
| 2018/0330518 | A1 | 11/2018 | Choi |
| 2021/0251610 | A1 | 8/2021 | Stergiopoulos et al. |

(Continued)

OTHER PUBLICATIONS

"Final Office Action", U.S. Appl. No. 18/182,196, Jul. 3, 2025, 23 pages.

(Continued)

*Primary Examiner* — Joseph M Santos Rodriguez
(74) *Attorney, Agent, or Firm* — Colby Nipper PLLC

(57) ABSTRACT

Systems and methods for anatomy-directed ultrasound are described. In some implementations, an anatomy-directed ultrasound system generates ultrasound data from an ultrasound scan of an anatomy, which is a bodily structure of an organism (e.g., human or animal). The system identifies organs represented in the ultrasound data and information associated with the organs including position and type of organ. Using this information, the system obtains or generates new ultrasound data that includes a region in which an item of interest is likely to be located. For example, the system can crop the original ultrasound data, refocus the ultrasound scan (e.g., by adjusting imaging parameters) to image the region that is likely to include the item of interest, or generate a weight map indicating the region. The anatomy-directed ultrasound system can increase accuracy and reduce the number of false positives in comparison to the number detected by conventional ultrasound systems.

20 Claims, 10 Drawing Sheets

100

(56) References Cited

U.S. PATENT DOCUMENTS

| | | | |
|---|---|---|---|
| 2022/0230310 | A1 | 7/2022 | Xie et al. |
| 2024/0299002 | A1 | 9/2024 | Dhatt et al. |

OTHER PUBLICATIONS

"Non-Final Office Action", U.S. Appl. No. 18/182,196, Jan. 30, 2025, 22 pages.

"Restriction Requirement", U.S. Appl. No. 18/182,196, filed Dec. 10, 2024, 11 pages.

400

500

600

700

ANATOMY-DIRECTED ULTRASOUND

CROSS-REFERENCE TO RELATED APPLICATION

This application is a division of and claims priority to U.S. Non-Provisional patent application Ser. No. 18/182,196, filed on Mar. 10, 2023, the disclosure of which is incorporated by reference herein in its entirety.

BACKGROUND

The accumulation of free fluid in a patient's body can be a life-threatening condition. Ultrasound systems, however, can be used to detect these free fluids. Ultrasound systems do so by transmitting sound waves at frequencies above the audible spectrum into a body, receiving echo signals caused by the sound waves reflecting from internal body parts, and converting the echo signals into electrical signals for image generation. For example, Focused Assessment with Sonography in Trauma (FAST) is a rapid bedside ultrasound examination that can be performed by emergency physicians and other healthcare professionals as a screening test for free fluid, including blood around the heart (pericardial effusion) or abdominal organs (hemoperitoneum).

Ultrasound operators, however, can miss the presence of free fluid, such as by interpreting that free fluid is fatty tissue between organs within a patient. In other cases, an ultrasound operator can misidentify fat as free fluid, resulting in a false positive. In still other cases, the ultrasound operator can misclassify an amount of free fluid in a patient. When the amount of free fluid is underestimated, the patient may not be given necessary care to remove the free fluid. When the amount of free fluid is overestimated, the patient may undergo a procedure to remove the free fluid, which may not be necessary. In still other cases, because of distractions in the environment, the ultrasound operator may miss free fluid in the patient, particularly if they are scanning quickly or if they are not directly looking for free fluid. In each of these cases, the patient may not receive the best care possible.

SUMMARY

Systems and methods for anatomy-directed ultrasound are described. In some implementations, an anatomy-directed ultrasound system generates ultrasound data from an ultrasound scan of an anatomy, which is a bodily structure of an organism (e.g., a human or an animal). The system identifies organs represented in the ultrasound data and information associated with the organs, including position and type of organ. Using this information, the system obtains or generates new ultrasound data that includes a region in which an item of interest is likely to be located. For example, the system can crop the original ultrasound data, refocus the ultrasound scan (e.g., by adjusting imaging parameters) to image the region that is likely to include the item of interest, or generate a weight map indicating the region. The anatomy-directed ultrasound system can increase accuracy or reduce the number of false positives in comparison to the number detected by conventional ultrasound systems.

In some aspects, an ultrasound system is disclosed. The ultrasound system includes an ultrasound scanner, one or more computer processors, and one or more computer-readable media. The ultrasound scanner is configured to generate ultrasound data based on reflections of ultrasound signals transmitted by the ultrasound scanner at an anatomy. The one or more computer-readable media have instructions stored thereon that, responsive to execution by the one or more computer processors, implement one or more modules. The one or more modules are configured to: identify one or more bodily structures and corresponding locations of the one or more bodily structures based on the ultrasound data; determine, based on the identified one or more bodily structures and the corresponding locations, a region having an item of interest proximate to, or associated with, at least one bodily structure of the identified one or more bodily structures; determine, based on a portion of the ultrasound data associated with the region or second ultrasound data, information corresponding to the region having the item of interest; and generate, based on the determined information, focused ultrasound data that includes the item of interest.

In some aspects, a method for anatomy-directed ultrasound is disclosed. The method includes receiving first ultrasound data generated by an ultrasound scanner based on reflections of ultrasound signals transmitted by the ultrasound scanner at an anatomy. The method also includes identifying one or more bodily structures represented in the first ultrasound data and determining anatomy information associated with the identified one or more bodily structures in the first ultrasound data. In addition, the method includes determining, based on the anatomy information, a region of interest in the first ultrasound data that is likely to include an item of interest. The method further includes generating second ultrasound data that is focused on the region of interest. Also, the method includes identifying the item of interest and a boundary enclosing the item of interest based on the second ultrasound data. Additionally, the method includes segmenting the item of interest from the second ultrasound data based on the boundary. Further, the method includes generating an output image having a segmentation of the item of interest.

Other systems, machines, and methods to provide anatomy-directed ultrasound are also described.

BRIEF DESCRIPTION OF THE DRAWINGS

The appended drawings illustrate examples and are, therefore, exemplary embodiments and not considered to be limiting in scope.

DETAILED DESCRIPTION

Figure 1:
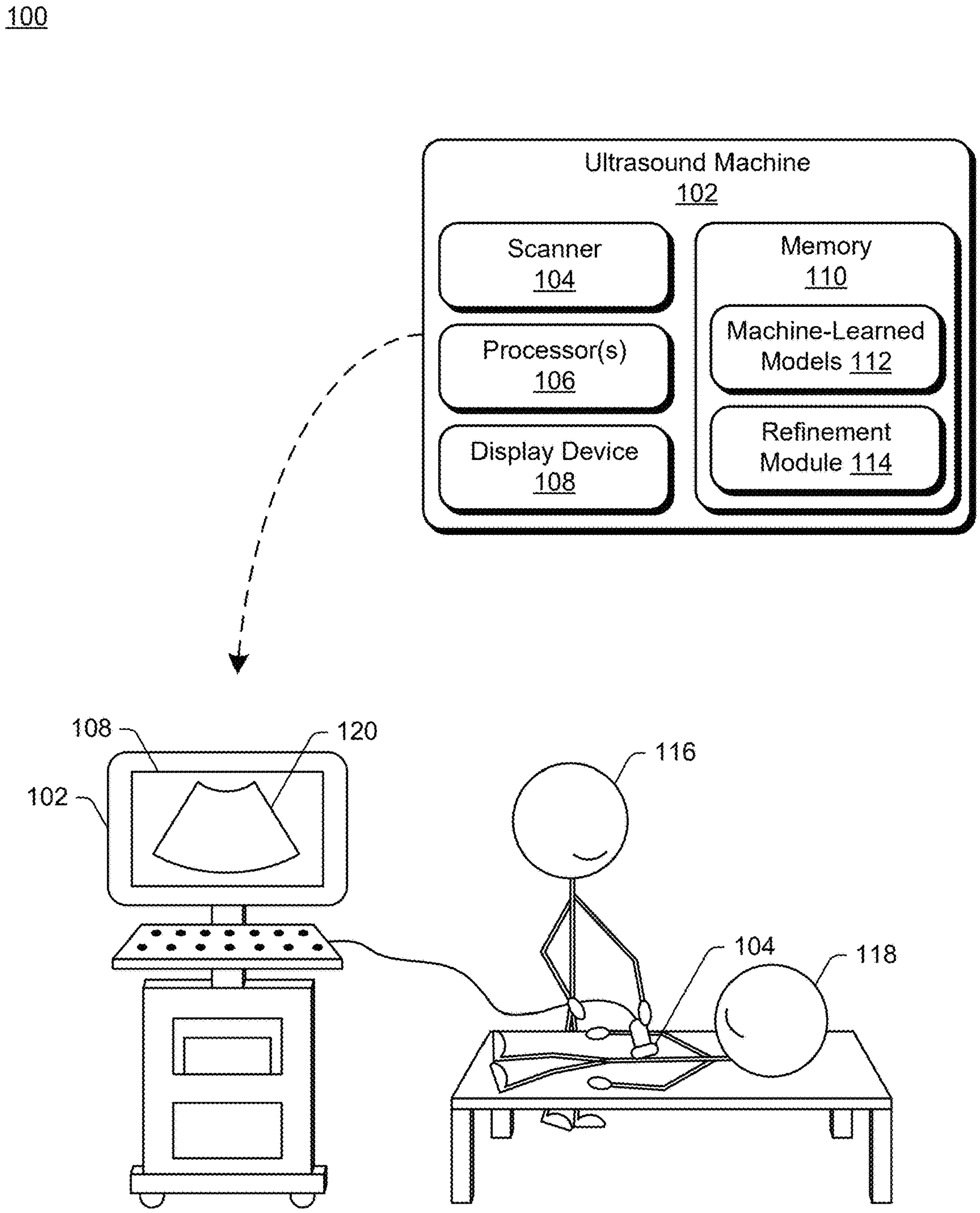
FIG. 1 illustrates an example environment for an anatomy-directed ultrasound system in accordance with one or more implementations.

Conventional ultrasound systems and operators of the systems can introduce errors when detecting the presence of issues in the body of a patient, resulting in the patient receiving less than the best possible care. Accordingly, systems, devices, and techniques are disclosed herein for anatomy-directed ultrasound. The techniques described herein can be implemented to detect an item of interest (e.g., free fluid, foreign object, abnormality, a part of an organ, or an undesired condition) in ultrasound data based on anatomy information (e.g., organ information) identified in the ultrasound data. In one example, techniques are described herein for detecting free fluid with ultrasound based on positions of organs. Such systems, devices, and techniques can also be used to classify the detected free fluid, for example, by type or amount. By understanding (i) which bodily structures (e.g., organs) are represented in the ultrasound data, (ii) respective locations of the represented bodily structures, and (iii) regions proximate or adjacent to the represented bodily structures where particular items of interest tend to be located, a suitably trained model (e.g., machine-learned model, neural network, or algorithm) can focus its attention such that the model ignores false positives outside the regions and finds items of interest with greater accuracy. The techniques described herein use information associated with organs (e.g., organs identified in ultrasound data, organ type, organ location in the ultrasound data, etc.); however, these techniques are applicable to any suitable bodily structure of a human or an animal. Thus, the term organ is used herein as a non-limiting example of a bodily structure.

In an example, the ultrasound system includes one or more machine-learned (ML) models (e.g., neural networks) that are implemented to process ultrasound data (e.g., ultrasound image, or data representing the ultrasound image) and determine a position and type of bodily structures in the ultrasound data. Some example ML models are described relative to FIG. 8. Based on the position and type of a bodily structure in the ultrasound data, the ultrasound system can generate additional ultrasound data that includes or is focused on a region in which an item of interest is likely to be located.

In one example, the ultrasound system uses the organ type and position in the ultrasound data to generate additional ultrasound data narrowed to a region in which free fluid is likely or tends to accumulate such as adjacent to an organ or between two organs (e.g., between a spleen and a kidney, between a liver and the kidney, or adjacent to a bladder). For instance, the ultrasound system can crop the original ultrasound data to refine the ultrasound data (e.g., to focus on only a portion of the ultrasound data). Additionally or alternatively, the ultrasound system can refocus the ultrasound by adjusting imaging parameters (gain, depth, beamformer parameters, etc.) to image the region, which is near an organ and likely to accumulate the free fluid. The ultrasound system can then process the additional ultrasound data with one or more ML models to segment the free fluid and thus determine the presence, absence, and/or amount of free fluid. Hence, the ultrasound system is anatomy-directed or organ-directed to determine free fluid.

The systems and techniques described herein are generally described with respect to detection of free fluid based on organ identification in ultrasound data. However, these systems and techniques can be also used to detect other items of interest in an organism and are not limited to detection of free fluid. An example includes detecting, based on detection of a first organ type and location, a second organ. Another example includes detecting a medical implant (e.g., stent, pacemaker, cardioverter-defibrillator, etc.). An expectation of where the implant should be located, based on the anatomy around the implant, and/or an expectation of the geometry of the implant can help locate and identify the implant. In another example, a lesion can be searched for and detected on an organ based on detection of the organ itself. For instance, the system can search a particular area of a kidney where lesions typically form (e.g., cancer) based on locating and identifying the kidney in the ultrasound image. In another example, the system can search for plaque in a carotid artery after first locating and identifying the artery.

In an example, the system can identify a first part of a bone and then search for a second part of the bone (e.g., search for one knuckle based on an image of another knuckle of a finger or toe). In another example, the system can search for a particular joint based on identification of another joint. Another example includes the system searching for an undesired condition or property indicative of a problem (e.g., search for surface roughness on a bone of a joint to determine arthritis). The system can use the described techniques to identify a rib to then search for the presence of Pneumothorax (PTX) (the presence of air or gas in the cavity between the lungs and the chest wall, causing collapse of the lung).

In another example, the system can recognize an aorta in the ultrasound image and then search for an abdominal aortic aneurysm along the aorta. The system can identify an ovary and fallopian tube and then focus on a particular area to search for a potential abnormality, such as an ectopic pregnancy (e.g., when a fertilized egg gets stuck on its way to the uterus, often due to the fallopian tube being damaged by inflammation or being misshapen) or an ovarian cyst. In a prenatal circumstance, the system can search for an issue or item of interest on the child (e.g., fetus) based on finding an issue or item of interest on the mother, or vice versa.

These are but some of many example uses of the techniques described herein, others include detecting aneurysms, foreign objects, and other abnormalities.

Anatomy-Directed Ultrasound System

FIG. 1 illustrates an example environment for an anatomy-directed ultrasound system 100 in accordance with one or more implementations. The ultrasound system 100 is anatomy-directed to determine an item of interest (e.g., free fluid, foreign object, abnormality, particular anatomy part, etc.). Generally, the ultrasound system 100 includes an ultrasound machine 102, which generates data (including images) based on high-frequency sound waves reflecting off body structures. The ultrasound machine 102 includes various components, some of which include a scanner 104, one or more processors 106, a display device 108, and a memory 110. In an example, the display device 108 can include multiple display devices. A first display device can display a first ultrasound image, and a second display device can display a focused ultrasound image or a segmentation image that is generated based on the first ultrasound image. In some implementations, the ultrasound machine 102 also includes one or more ML models 112 and a refinement module 114 configured to provide input to and/or manipulate output of one or more of the ML models 112.

A user 116 (e.g., nurse, ultrasound technician, operator, sonographer, etc.) directs the scanner 104 toward a patient 118 to non-invasively scan internal bodily structures (e.g., organs, tissues, etc.) of the patient 118 for testing, diagnostic, or therapeutic reasons. In some implementations, the scanner 104 includes an ultrasound transducer array and electronics coupled to the ultrasound transducer array to transmit ultrasound signals to the patient's anatomy and receive ultrasound signals reflected from the patient's anatomy. In some implementations, the scanner 104 is an ultrasound scanner, which can also be referred to as an ultrasound probe.

The display device 108 is coupled to the processor 106, which processes the reflected ultrasound signals to generate ultrasound data. The display device is configured to generate and display an ultrasound image (e.g., ultrasound image 120) of the anatomy based on the ultrasound data generated by the processor 106 from the reflected ultrasound signals detected by the scanner 104. In aspects, the ultrasound data can include data and/or the ultrasound image 120. In some embodiments, the ultrasound data (e.g., the ultrasound image 120, or data representing the ultrasound image 120) is used as input to at least one ML model 112 implemented to identify parts of the anatomy scanned by the scanner 104. For example, one ML model 112 can identify one or more organs (including by type) in the ultrasound data and a corresponding location (e.g., position) of each identified organ in the ultrasound data.

Based on the type and position of an organ, the ultrasound system 100 generates, using at least the refinement module 114, new ultrasound data that includes a region in which a particular item of interest (e.g., free fluid) is likely to be located (e.g., adjacent to an organ, between two organs, or on a different part of an organ). For example, the refinement module 114 can crop the original ultrasound data (e.g., the ultrasound image 120), generate imaging parameters to refocus the scanner 104 to scan the region that is likely (e.g., has a probability greater than a threshold value) to include the item of interest, or generate a weight map indicating the region that is likely to include the item of interest. Another ML model 112 can be implemented to use the new ultrasound data as input to determine whether the item of interest exists in the region and, if the item of interest is detected, generate a segmentation of the item of interest. In some implementations, the segmentation can be displayed in an image via the display device 108, either concurrently with or independent of the ultrasound image 120. Further details of these and other features are described below.

Figure 2:
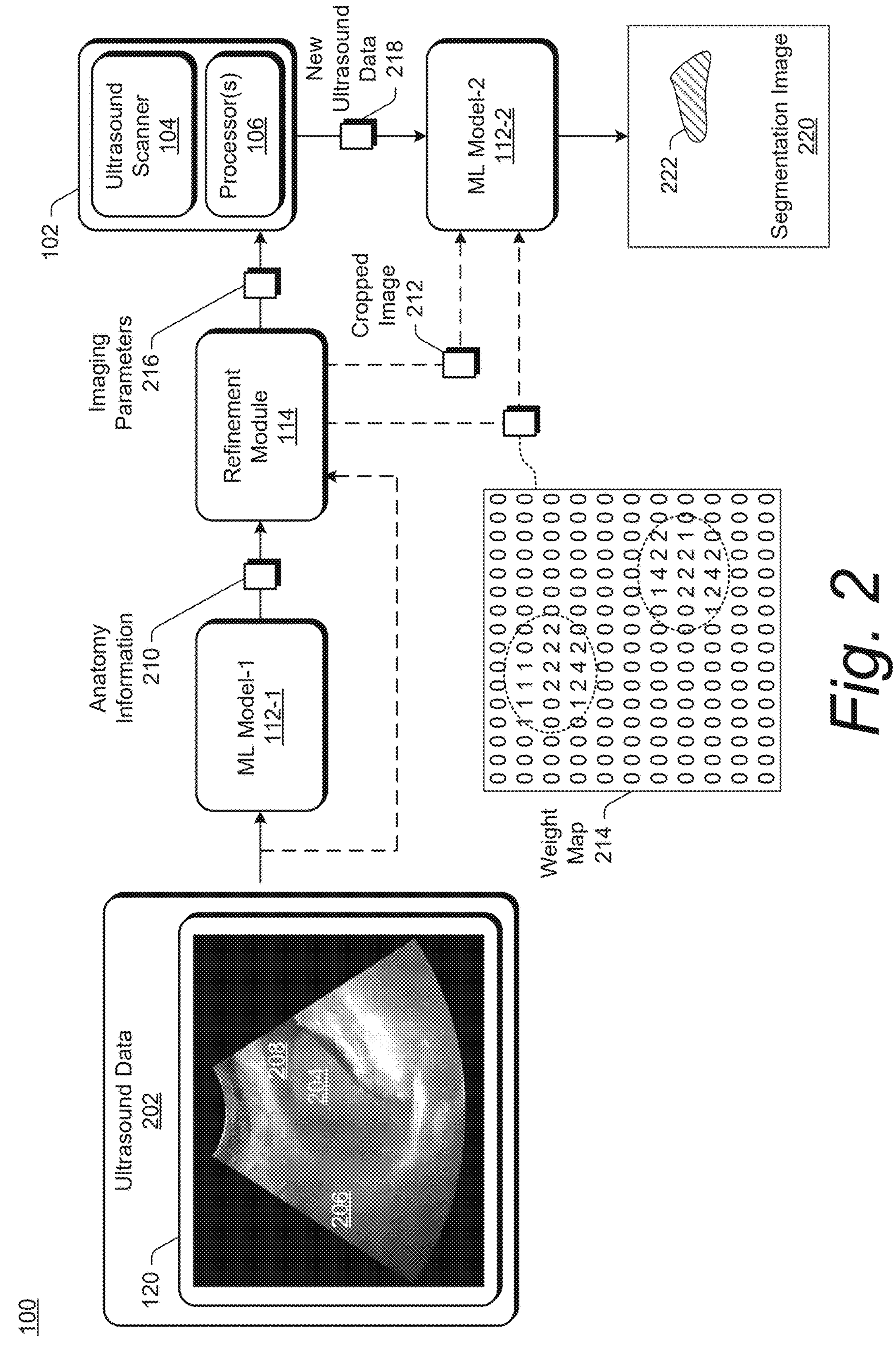
FIG. 2 illustrates an example anatomy-directed ultrasound system in accordance with one or more implementations.

FIG. 2 illustrates an example anatomy-directed ultrasound system 100 in accordance with one or more implementations. The ultrasound system 100 is anatomy-directed to determine an item of interest (e.g., free fluid, foreign object, abnormality, particular anatomy part, etc.). The ultrasound system 100 includes a first ML model 112-1 (ML Model-1 112-1) that is implemented at least partially in hardware of a computing device, such as a tablet coupled to an ultrasound scanner (e.g., the scanner 104), an ultrasound machine (e.g., ultrasound machine 102), and the like. Ultrasound data 202 (e.g., the ultrasound image 120, or data representing the ultrasound image 120) is used as input to the first ML model 112-1. As described herein, ultrasound data 202 includes data generated by the processor 106 based on the reflected ultrasound signals detected by the scanner 104. In the illustrated example, the ultrasound image 120 depicts a kidney 204, a spleen 206, and free fluid 208. The first ML model 112-1 processes the ultrasound image 120 to generate anatomy information 210 including locations and types of organs identified in the ultrasound image 120 (e.g., the kidney 204 and the spleen 206).

The first ML model 112-1 can be any suitable ML model, including a neural network. Further, the first ML model 112-1 can generate the anatomy information 210 in any suitable way. In one example, the first ML model 112-1 generates a segmentation of the organs (e.g., data or an image that indicates pixels with a first color that belong to the organ locations and pixels with a second color that do not belong to the organ locations) and labels that classify the organs by type, such as a liver label, a kidney label, etc. Additionally or alternatively, the first ML model 112-1 can generate coordinates (e.g., Cartesian coordinates) that indicate the locations of the organs in the ultrasound image 120.

Generating organ locations can include fitting a geometric shape to an identified organ, such as by generating a centroid (e.g., a center position) for an organ and a radius of a circle that is centered at the centroid and encloses the organ. Hence, when an additional image is generated based on the organ locations (e.g., by cropping), the ultrasound system 100 can generate the additional image to include at least part of the area enclosed by the circle to provide a visual frame of reference of the item of interest (e.g., free fluid) relative to the organ. Moreover, parameters of a geometric shape (e.g., the center and radius of a circle, or the center and radii of major and minor axes of an ellipse) represent a small amount of information compared to a more precise segmentation of an organ, and this small amount of information may be sufficient to guide the ultrasound system 100 to search for free fluid or other items of interest in proximity to the identified organ.

Accordingly, it may be more efficient and effective to train an ML model to search for an item of interest near an organ based on parameters of a geometric shape when compared to training the ML model based on more accurate segmentations of the organ. For instance, fewer training images (ground truth images) may be required to train the ML model to search for the item of interest in proximity to the organ based on the parameters of the geometric shape in comparison to using accurate segmentations of the organ. Moreover, the ML model 112 trained based on the parameters of the geometric shape can be more accurate and generate results more quickly than an ML model trained based on accurate segmentations of the organ.

The first ML model 112-1 provides the anatomy information 210 (e.g., organ locations and types) to the refinement module 114. The refinement module 114 is configured to refine the given data (e.g., ultrasound image, anatomy information, etc.) in various ways to provide refinement data usable as input to a second ML model 112-2 (ML Model 2 112-2) that is trained to identify the item of interest. Some examples of refinement data generated by the refinement module 114 include an additional image (e.g., a cropped image 212), a weight map 214, imaging parameters 216, and so forth.

In some implementations, the refinement module 114 refines the ultrasound data 202 by cropping the ultrasound image 120 based on the anatomy information 210, resulting in the cropped image 212. For example, the refinement module 114 can include a neural network to generate the cropped image 120, including to crop the ultrasound image 120 and center the expected location of the item of interest in the cropped image 120. By cropping the ultrasound image 120 and focusing on regions that are expected to contain the item of interest, the ultrasound system 100 can reduce the number of false positives, compared to ultrasound systems that search for an item of interest (e.g., free fluid) in regions where such item is not expected. Further, cropping the ultrasound image 120 can reduce the amount of computation needed to process the cropped image 212 by the second ML model 112-2, compared to processing an uncropped image.

Additionally or alternatively, the refinement module 114 can upsample the size of the additional image (e.g., cropped image 212) to match, for example, the size of the ultrasound image 120. For instance, the refinement module 114 can include a super-resolution processor to upsample the cropped image 212 to match the size of the ultrasound image 120. By upsampling the cropped image 212, the second ML model 112-2 that receives the cropped image 212 from the refinement module 114 can generate a better segmentation of the item of interest than without upsampling.

In an example, the refinement module 114 generates the weight map 214 (e.g., attention map) that places weights on regions of the ultrasound image 120 to help focus the segmentation process. The weight can be binary (e.g., a "0" to indicate a region of low interest, and a "1" to indicate a region of higher interest for the expected segmentation). The weight can correspond to one or more pixels of the ultrasound image 120. In an example, as illustrated in FIG. 1, the weight map can include multi-level values, with higher values corresponding to regions more likely to include the item of interest or the identified organ(s).

Additionally or alternatively, the refinement module 114 can generate imaging parameters 216 that the ultrasound system 100 can use to generate an additional image for detecting the item of interest. For example, the imaging parameters 216 generated by the refinement module 114 can include settings for gain, depth, examination type, beamform configuration, beamform intensity, beamform frequency, resolution, image size, image-center location, image quality, and so forth. The refinement module 114 can include a neural network, signal processor, database, and the like to generate the imaging parameters, based on at least one of the organ location, organ type, or ultrasound image 120.

The refinement module 114 then provides the imaging parameters 216 to the ultrasound machine 102, which can be configured according to the imaging parameters 216. In an example, the ultrasound system 100 automatically and without user intervention configures the ultrasound machine 102 based on the imaging parameters 216, including to automatically set at least one of a gain, a depth, an examination type, or beamform configurations. Using the newly set parameters, the ultrasound machine 102 generates a new ultrasound data 218 (e.g., an ultrasound image in addition to the ultrasound image 120) and provides the new ultrasound data 218 to the second ML model 112-2. The new ultrasound data 218 can be an image or ultrasound data representing the new ultrasound data 218 and can be used alone or in combination with prior ultrasound data (e.g., the ultrasound image 120).

In an example, setting image parameters can include changing an imaging mode. For instance, harmonic imaging can be enabled to help better image some items of interest, such as free fluid because harmonics generally build up faster in free fluid than in regular tissue. In some embodiments, the setting of the image parameters can increase the image quality (e.g., better resolution) of the item of interest and can decrease the image quality of the originally detected organ. Additionally or alternatively, setting the image parameters can cause the intensity of the ultrasound to be focused in areas where the item of interest is expected to be located. For example, when using contrast agents that have bubbles, imaging at standard intensities usually does not break the bubbles of the contrast agent. However, to better image free fluid, the intensity of the ultrasound can be increased in some areas, but not in others, to break the bubbles for imaging the free fluid.

In an example, setting the imaging parameters can include setting parameters for (e.g., enabling) an imaging mode other than ultrasound or in addition to ultrasound. For instance, a magnetic field can be perturbed to enable magnetic resonance imaging, which can be used to detect, for example, an implant, free fluid, or another item of interest.

In one example, a laser source is enabled to perform photoacoustic imaging (PAI). For instance, the laser source can cause tissue to vibrate and generate ultrasound, which can be detected with an ultrasound system. In another example, setting the imaging parameters can include changing an operating frequency of the ultrasound to affect a multifrequency examination, such as is described below with respect to free fluid classification.

As described above, the second ML model 112-2 can receive the weight map 214 from the refinement module 114 and use the weight map to generate focused ultrasound data (e.g., a segmentation image 220). As described, the weight map 214 includes numerical values (e.g., binary values, or non-binary values) that each correspond to an intensity of one or more reflected ultrasound signals. In some examples, a higher numerical value (e.g., "1" in a binary system) in the weight map 214 represents a region of the ultrasound image 120 of high interest, which may be a region having a high probability (e.g., a probability exceeding a threshold value of, for example, 0.7) of including an item of interest, such as free fluid. In such an example, higher values in the weight map 214 represent areas that have little to no reflected ultrasound signals in proximity to one or more identified organs in the anatomy information 210. Further, a lower numerical value (e.g., "0" in a binary system) can represent a region of low interest, which may be a region having a low probability (e.g., probability below a threshold value of, for example, 0.5) of including an item of interest, such as an expected bodily structure. A non-binary system may be used that includes a larger range of numerical values (e.g., 0-3, 0-4, 0-5, 0-6, 0-7, 0-8, 0-9) to represent various levels of interest in the ultrasound image 120. Accordingly, the higher values in the weight map 214 can represent areas that have a likelihood (e.g., statistical value or probability greater than a threshold value) of including a particular item of interest. For example, a value of 4 on a scale of 0-5 can indicate a region of interest with a relatively high probability of including an item of interest. In this way, the second ML model 112-2 can use the information in the weight map 214 to perform a narrower search for the item of interest in the regions of the ultrasound image 120 indicated by the weight map 214.

In another example, a low-numerical value in the weight map 214 (e.g., "0" in a binary system) represents an area of the ultrasound image 120 of low interest, such as a dark area of the ultrasound image 120 representing fluid. A high-numerical value in the weight map 214 (e.g., "1" in a binary system) represents an area of the ultrasound image 120 of high interest, such as a bright area of the ultrasound image 120 representing a part of an organ or other bodily structure. In an example using a non-binary system, a value of three on a scale of 0-7 can indicate a region that has some interest but has a relatively low confidence level (e.g., based on low image quality, corrupt ultrasound data, etc.). A higher value (e.g., six on the scale of 0-7) can indicate a region of higher interest based on a relatively high confidence level that the region represents an anatomy (e.g., an organ). In this example, the information in the weight map 214 can be used by the second ML model 112-2 to perform a narrower search for the item of interest in regions of the ultrasound image 120 near anatomy boundaries indicated by the weight map 214.

In an example, the refinement module 114 generates guidance for an operator of the ultrasound system 100 based on at least one of the organ location, organ type, and ultrasound image 120. For example, the ultrasound system 100 can suggest, based on the organ type, to use a certain ultrasound scanner that is suitable for the organ type. The guidance can also include instructions on how to move the scanner to obtain a better view. The guidance can be exposed by the ultrasound machine 102, such as via a clinical display, audio broadcast via a speaker, etc.

By using at least one of the cropped image 212, the weight map 214, or the new ultrasound data 218, the second ML model 112-2 generates an output data (e.g., the segmentation image 220, or segmentation data representing the segmentation image 220) that includes a segmentation 222 of the item of interest (e.g., the free fluid 208). In aspects, the segmentation 222 may be focused ultrasound data. Additionally or alternatively (and not shown for clarity in FIG. 1), the segmentation image 220 can include segmentations of organs, such as the kidney 204 and the spleen 206. The second ML model 112-2 can reposition the segmentation 222 according to a coordinate system of the ultrasound image 120 so that the segmentation 222 of the item of interest is in a same position and orientation in the segmentation image 220 as the item of interest is in the ultrasound image 120. The segmentation image 220 can be scaled to align the item of interest with the ultrasound data 202. In this way, the segmentation 222 can be scaled to match the size of the item of interest (e.g., the free fluid 208) in the ultrasound image 120. Such scaling may enable the segmentation image 220 to be displayed concurrently (e.g., overlaid, side-by-side) with the ultrasound image 120 to highlight or emphasize the item of interest in the ultrasound image 120.

In an example, visual parameters for display of the segmentations can be user selected. For example, the user can select a visual parameter such as fill patterns and/or colors, line patterns and/or colors, and the like. Hence, the user can configure the display so that the segmentations can be easily distinguished from one another and the background of the segmentation image 220. This flexibility is especially useful for color-blind operators.

In one example, the ultrasound system 100 can determine a distance between two organs identified in the ultrasound data, such as a distance between the kidney 204 and the spleen 206 in the ultrasound image 120. For example, the ultrasound system 100 can include (not shown for clarity in FIG. 2) a pre-process module that processes the ultrasound data 202 before it is provided to the blocks shown in FIG. 2. In an implementation for detecting free fluid, the pre-process module can determine a distance between organs, and if the distance is below a threshold distance, such as 0.1 mm, then the pre-process module can prevent the ultrasound image from being provided to the blocks illustrated in FIG. 2 so that a segmentation of free fluid is not generated. This inhibition, when the threshold condition is satisfied, is an advantage because it can prevent false positives from being generated and can save on resources (e.g., compute resources, power draw, and time).

In one example, the ultrasound system 100 suppresses the display of the segmentation 222 of free fluid when the segmentation 222 is in a region that is known to not contain free fluid or is not likely to contain free fluid. This suppression can occur even if the system generates the segmentation inside the region and can prevent false positives from being displayed. For instance, rather than corresponding to free fluid, the detection may correspond to a fluid-filled cyst or blood in a vein or artery. One example of such a region is the interior of blood vessels. Another example includes cysts, which can be simple or complex and can occur in any organ (kidney, liver, spleen, pancreas, ovaries, etc.).

Another example includes an effusion, which occurs in the heart (pericardial) and lungs (pleural). Less common examples include biliary duct enlargement, extrarenal pelvis, ureter enlargement, aortic aneurysm, hydronephrosis, enlarged lymph nodes, cholecystitis, dilated abdominal and/or pelvic veins (inferior vena cava, portal vein, recanalized umbilical, etc.), gastrointestinal fluids (stomach and bowel), hematomas, and incarcerations (trapped tissue). Other regions can include bone and air. Similar regions may be detected in pelvic exams. The ultrasound system 100 can determine regions that do not, or are unlikely to, contain free fluid based on a database of regions, the ultrasound data 202, the ultrasound image 120, the anatomy information (e.g., locations, types), or combinations thereof.

The determination of a region that is likely to include an item of interest can be based on probability. Probabilities associated with various regions can be determined from a collection of data. The probabilities can represent a tendency of the item of interest to be present in the particular region based on a number of times the item of interest is found to be present in the particular region in the collection of data. In this way, the probabilities also represent a likelihood of the item of interest being present in ultrasound data generated from an ultrasound scan of an anatomy of a current patient. For example, free fluid tends to accumulate in the abdomen between the liver and the kidney but not inside the kidney. In another example, cysts tend to occur on or in an organ (e.g., kidney, liver, spleen, etc.) but not in tissue between organs. Accordingly, a region that is likely to include the item of interest is a region having a probability greater than a threshold value (e.g., 0.6, 0.65, 0.7, 0.75, 0.8), where the probability is based on at least a collection of ultrasound data, images, labels, or any combination thereof.

The processing blocks of the ultrasound system 100 in FIG. 2 are examples and can be combined or separated in any suitable way. For example, the first ML model 112-1, the second ML model 112-2, and a third ML model (e.g., neural network) of the refinement module 114 can be combined into one or more ML models. In an example, the processing blocks or ML Models (or networks) can be combined into a single ML model with multiple layers that are initially trained to identify organs. Final layers of this ML model can then be changed to identify just the item of interest (e.g., free fluid).

In another implementation, the ultrasound data 202 includes a series of ultrasound images (e.g., frames forming a video clip). For example, the user 116 fans through a region of the patient's anatomy, by adjusting the orientation of the scanner 104 relative to the patient's anatomy and/or adjusting parameters (e.g., depth, gain, beamformer parameters, etc.) of the scanner 104 to create a video clip. The frames of the video clip are then processed by the first ML model 112-1, which identifies the anatomy information 210 in some (including all) of the frames of the video clip. The refinement module 114 refines the video clip by generating a weight map (e.g., the weight map 214) for one or more frames of the video clip based on the anatomy information 210 or by cropping one or more frames of the video clip based on the anatomy information 210 to enable the second ML model 112-2 to focus on regions expected to contain an item of interest. This refined information (e.g., weight map(s) or cropped frame(s)) is processed by the second ML model 112-2 and the second ML model 112-2 identifies and selects a frame from the video clip that best represents the item of interest. In some aspects, the second ML model 112-2 can also segment the item of interest from the selected frame and provide output data (e.g., the segmentation image 220, or segmentation data representing the segmentation image 220) having the segmentation 222 of the item of interest (e.g., the free fluid 208). In some implementations, the second ML model 112-2 can determine and provide a likelihood (e.g., probability greater than a threshold value) of the item of interest being present in the video clip. Alternatively, the likelihood of the item of interest being present in the video clip can be determined and provided by the refinement module 114. Although this example is described in the context of free fluid detection, various items of interest can be identified and segmented from one or more frames of a video clip of ultrasound data, some examples of which are described herein.

Figure 3:
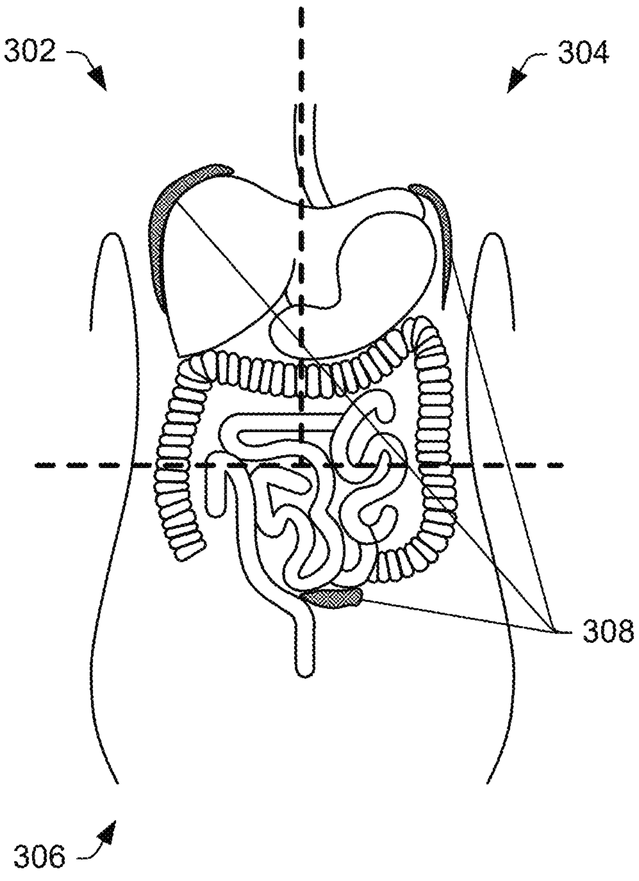
FIG. 3 illustrates regions of an example examination of a patient's torso.

Consider FIG. 3, which illustrates regions of an example examination of a patient's torso 300. In implementations, a FAST examination of the patient's torso 300 typically divides into three quadrants: a right upper quadrant (RUQ) 302, a left upper quadrant (LUQ) 304, and a pelvic region (PEL) 306. These are areas of the abdomen where free fluid 308 (e.g., free fluid 208 from FIG. 2) tends to accumulate. The ultrasound system 100 can include separate models (e.g., ML models, neural networks) for each quadrant. In an example, a first model can be used to recognize which quadrant is being examined, and then the ultrasound system 100 can select an RUQ model, an LEQ model, or a PEL model based on the quadrant being examined.

Figure 4:
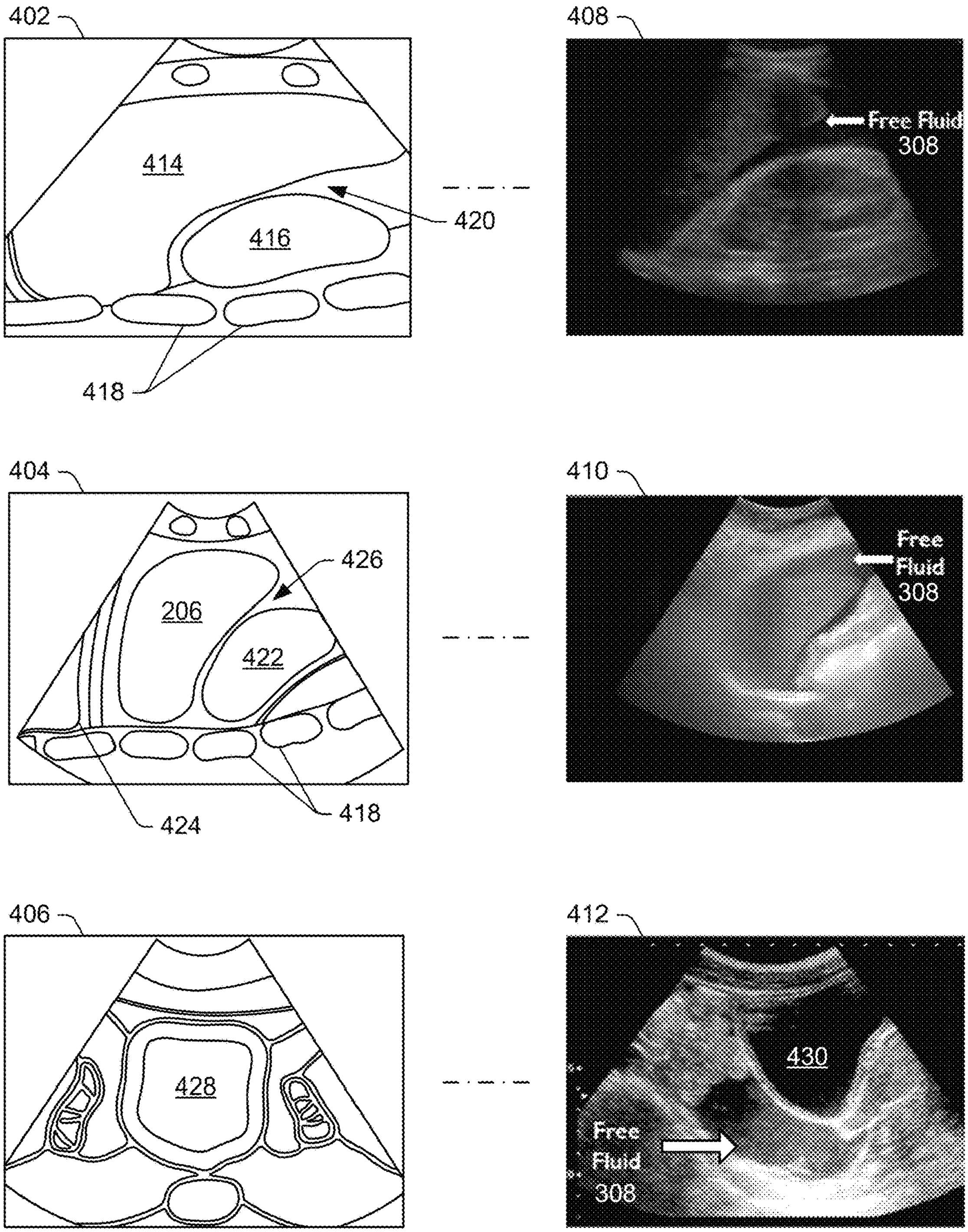
FIG. 4 illustrates examples of free fluid detection.

Continuing, FIG. 4 illustrates examples 400 of free fluid detection. The examples 400 include schematics and ultrasound images generated as part of a Focused Assessment with Sonography in Trauma (FAST) examination. The schematics include an RUQ schematic 402, an LUQ schematic 404, and a PEL schematic 406. The ultrasound images include an RUQ image 408, an LUQ image 410, and a PEL image 412. The RUQ schematic 402 includes a depiction of a liver 414, a right kidney 416, and portions of a spine 418. Also included in the RUQ schematic 402 is an indication of a region 420 or an area where free fluid (e.g., free fluid 308) tends to accumulate in the abdomen (e.g., between the liver 414 and the right kidney 416). In the corresponding ultrasound image (e.g., the RUQ image 408), a dark area or band exists between two more echoic (e.g., of or like an echo) areas. The more echoic areas (e.g., brighter areas) represent the liver 414 and the right kidney 416 while the dark area represents the free fluid 308 because free fluid is generally detected as anechoic (e.g., free from echo).

The LUQ schematic 404 depicts the spleen 206, a left kidney 422, a left lung 424, and portions of the spine 418. Also included in the LUQ schematic 404 is an indication of an additional region where free fluid tends to accumulate in the abdomen. For example, free fluid tends to accumulate in a region 426, which is between the spleen 206 and the left kidney 422. In the corresponding ultrasound image (e.g., the LUQ image 410) of the LUQ, an anechoic area or less echoic area between two more echoic areas (e.g., areas known to represent the spleen 206 and the left kidney 422) indicates the existence of free fluid 308. It is noted that in some cases such as this LUQ image 410, the free fluid 308 is not as obvious, for example, as it is in the RUQ image 408. Rather, the free fluid 308 in the LUQ image 410 is a more subtle presentation. This difference can make detection of free fluid more challenging.

The PEL schematic 406 depicts a bladder 428. The corresponding ultrasound image (e.g., the PEL image 412) includes a large dark area 430, which is an anechoic area representing fluid. However, this particular fluid is not free fluid because it is contained within the bladder 428 and is therefore contained fluid. Free fluid is fluid accumulating outside of organs in an area where it should not be accumulating. In the PEL image 412, a collection of free fluid 308 is detected below the bladder 428.

Accordingly, detection of an item of interest such as free fluid can be challenging based on only a visual examination. For example, unwanted free fluid is not necessarily presented as dark or anechoic areas (e.g., the free fluid 308 may be presented as slightly echoic such as in the LUQ image 410), and some dark or anechoic areas are not necessarily free fluid (e.g., the dark area 430 is contained fluid inside the bladder 428). Other items of interest may also be difficult to identify for similar reasons. Consequently, directing the detection of items of interest based first on anatomy detection (e.g., focusing a search in areas that are likely to include the item of interest) enhances the accuracy of detection of items of interest and reduces detection and display of false positives.

Figure 5:
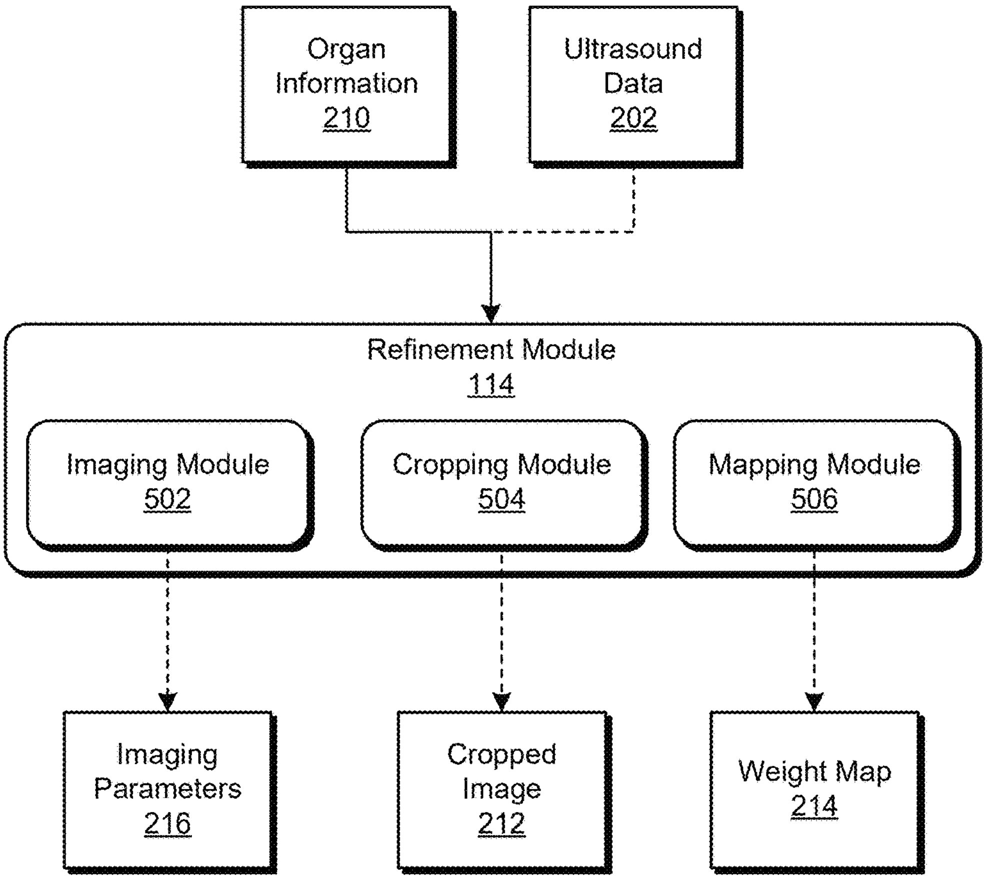
FIG. 5 illustrates an example implementation of a refinement module from FIG. 1 in more detail.

FIG. 5 illustrates an example implementation 500 of the refinement module 114 from FIG. 1 in more detail. For example, the refinement module 114 can include various modules such as an imaging module 502, a cropping module 504, and a mapping module 506. The refinement module 114 uses the anatomy information 210 and the ultrasound data 202 as input to provide refinement data usable as input to an ML model (e.g., the ML Model-2 112-2 shown in FIG. 2).

For example, the imaging module 502 can set or adjust imaging parameters (e.g., the imaging parameters 216) for an ultrasound machine (e.g., the ultrasound machine 102 in FIG. 2) to enable the ultrasound machine to generate new ultrasound data that is focused on a region that is likely to include an item of interest. The adjusted imaging parameters can enable image quality to be increased, cause the intensity of an ultrasound scan to be focused in areas where the item of interest is likely to be present, change an imaging mode of the ultrasound machine, change an operating frequency of the ultrasound to affect a multi-frequency examination, and so forth.

The cropping module 504 is configured to generate a cropped image (e.g., the cropped image 212), which is a cropped version of the ultrasound data 202 based on the anatomy information 210. In an example, the cropped image 212 is cropped to center or focus the cropped image 212 on the region where the item of interest is likely to be present and to remove regions where the item of interest is not likely to be present. In some aspects, the cropping module 504 is configured to generate cropped data, which is a subset of the ultrasound data 202 that includes the region where the item of interest is likely to be located and excludes regions where the item of interest is not likely to be located.

The mapping module 506 is configured to generate a weight map (e.g., the weight map 214), which uses weighted values (including zero) to identify regions of interest in the ultrasound data 202. In an example, the weighted values indicate a region where the item of interest is likely to be located. In another example, the weighted values indicate where at least one organ in the ultrasound data 202 is located. The weight map 214 enables an ML model (e.g., the ML Model-2 112-2 in FIG. 2) to refine, narrow, or focus its search for the item of interest in the ultrasound data 202, which increases efficiency and reduces computational and processing costs.

Free Fluid Classification

In some embodiments, the ultrasound system 100 can determine a classification of the item of interest, such as the free fluid, that classifies a type of the item of interest. Classifications of free fluid, for example, can include blood, inter-cellular fluid, and urine. In one example, the classifications are binary (e.g., blood and non-blood fluids). The ultrasound system can generate a classification for the free fluid based on any suitable data. For instance, the classification can be based on a location of the free fluid relative to one or more organs.

In one example, the ultrasound system is configured in a Doppler mode that can detect echoes from red blood cells. When detected, the echoes can be used to classify the free fluid as blood. When the echoes are not detected from the red blood cells, the ultrasound system can classify the free fluid as a non-blood fluid. Generally, the fluid (e.g., blood) is better resolved with motion when using the Doppler mode. In an example, the flow is induced as part of the procedure (e.g., by moving the patient or applying pressure with the ultrasound scanner to move the fluid).

In an example, precise movement of the fluid alone can be determined by removing a component of movement of the ultrasound scanner (such as by subtraction). For instance, the ultrasound scanner 104 can include an inertial measurement unit (IMU) that can determine a location and orientation of the ultrasound scanner 104 (e.g., in a coordinate system of a registration system). An IMU can include a combination of accelerometers, gyroscopes, and magnetometers and generate location and/or orientation data including data representing six degrees of freedom (6DOF), such as yaw, pitch, and roll angles in a coordinate system. Typically, 6DOF refers to the freedom of movement of a body in three-dimensional space. For example, the body is free to change position as forward/backward (surge), up/down (heave), and left/right (sway) translation in three perpendicular axes, combined with changes in orientation through rotation about three perpendicular axes, often termed yaw (normal axis), pitch (transverse axis), and roll (longitudinal axis). Additionally or alternatively, the ultrasound system can include a camera to determine location and/or orientation data for the ultrasound scanner. The precise movement of the fluid can be determined by measuring a movement of the fluid via the ultrasound scanner 104 and removing from the measurement (e.g., subtracting out of it) movement of the ultrasound scanner 104 itself determined from the IMU.

Additionally or alternatively, the ultrasound system 100 can determine an elasticity (e.g., clastic property) of the free fluid and determine a classification of the free fluid based on the elasticity. For example, pressure can be applied to an area of free fluid, such as with the ultrasound scanner 104, and an amount of compression under the pressure and rate of rebound when the pressure is removed can be determined from the reflected ultrasound. The type of free fluid can be determined from the elasticity (e.g., compression and rebound). For instance, blood can have a first set of elastic properties and extracellular fluid (e.g., ascites) can have another set of elastic properties. Moreover, the ultrasound system 100 can use the elasticity properties to distinguish free fluid from an organ or other bodily structure.

In an example, the type of fluid can be determined from a pattern in the ultrasound image 120. For instance, when pressure from the ultrasound scanner 104 is applied to blood (e.g., static blood), a swirl pattern is typically observed in the ultrasound image 120. Hence, if this swirl pattern is observed, the free fluid can be determined to be blood, and if the swirl pattern is not observed, the free fluid can be determined to be a non-blood fluid, such as pus or urine, or even not blood but a clot, such as a thrombus. A degree of blood coagulation can be determined from an edge analysis of the fluid. For instance, as static blood starts to coagulate, it becomes more echogenic, which enables its edges to be more readily imaged.

Additionally or alternatively, the ultrasound system 100 can determine a classification of the free fluid based on a frequency of the ultrasound. For instance, blood behaves differently at high-frequency ultrasound versus low-frequency ultrasound. At higher-frequency ultrasound (e.g., greater than 20 MHZ), the ultrasound distinguishes red blood cells of blood, whereas at lower-frequency ultrasound (e.g., less than 20 MHz), the blood tends to appear dark (e.g., black) in the ultrasound image 120. For non-blood free fluids, both low- and high-frequency ultrasound do not detect red blood cells. Hence, the ultrasound system 100 can implement a multi-frequency ultrasound examination (e.g., separately with high- and low-frequency ultrasound) and, based on the results, classify the free fluid as blood or non-blood fluid.

Additionally or alternatively, the ultrasound system 100 can selectively acquire radio-frequency (RF) data (e.g., high-resolution, undecimated, unprocessed, beamformed data at a full acquisition sampling rate) at either a high frequency or a low frequency and use that RF data to perform higher-resolution tissue analysis. This may enable more detailed analysis of different tissue types and fluids, which can exhibit different spectral patterns than structured tissue. A location of RF data acquisition can be guided by information such as organ placement, as determined on the lower-resolution acquisition image.

The systems disclosed herein constitute numerous improvements over conventional ultrasound systems that do not detect items of interest, including free fluid, based on organ locations. For example, the systems disclosed herein can prevent or reduce detection of false positives by generating, based on organ locations, ultrasound data (including ultrasound images) that includes regions where free fluid is likely to accumulate and that does not include regions where free fluid is not likely to accumulate. In another example, the systems disclosed herein can prevent or reduce detection of false positives by generating, based on organ locations, ultrasound data (including ultrasound images) that includes regions where an item of interest is likely to be located and that does not include regions where the item of interest is not likely to be located. Moreover, the systems disclosed herein can prevent false positives from being displayed by suppressing the display of segmentations of the item of interest when they occur in regions that are not likely to include the item of interest.

In contrast, because conventional ultrasound systems do not generate, based on organ locations, ultrasound data or images that include regions where (i) an item of interest is likely to be located (or where free fluid is likely to accumulate) and (ii) that do not include regions where the item of interest is not likely to be located (or where free fluid is not likely to accumulate), the conventional ultrasound systems can display false positives (e.g., detection of free fluid when there is no free fluid, or detection of an item of interest where the item of interest is not present). Further, the systems disclosed herein can be easily and efficiently trained, because in some embodiments an accurate segmentation of an organ can be replaced with a geometric shape that is fit to the organ. Hence, fewer ground truth images may be used for training compared to in other ultrasound systems that require training with images containing accurate segmentations.

Example Methods

Methods 600 and 700 are shown as a set of blocks that specify operations performed but are not necessarily limited to the order or combinations shown for performing the operations by the respective blocks. Further, any of one or more of the operations can be repeated, combined, reorganized, or linked to provide a wide array of additional and/or alternate methods. In portions of the following discussion, reference may be made to the example system 100 of FIG. 1 or to entities or processes as detailed in FIGS. 2-6, reference to which is made for example only. The techniques are not limited to performance by one entity or multiple entities operating on one device.

Figure 6:
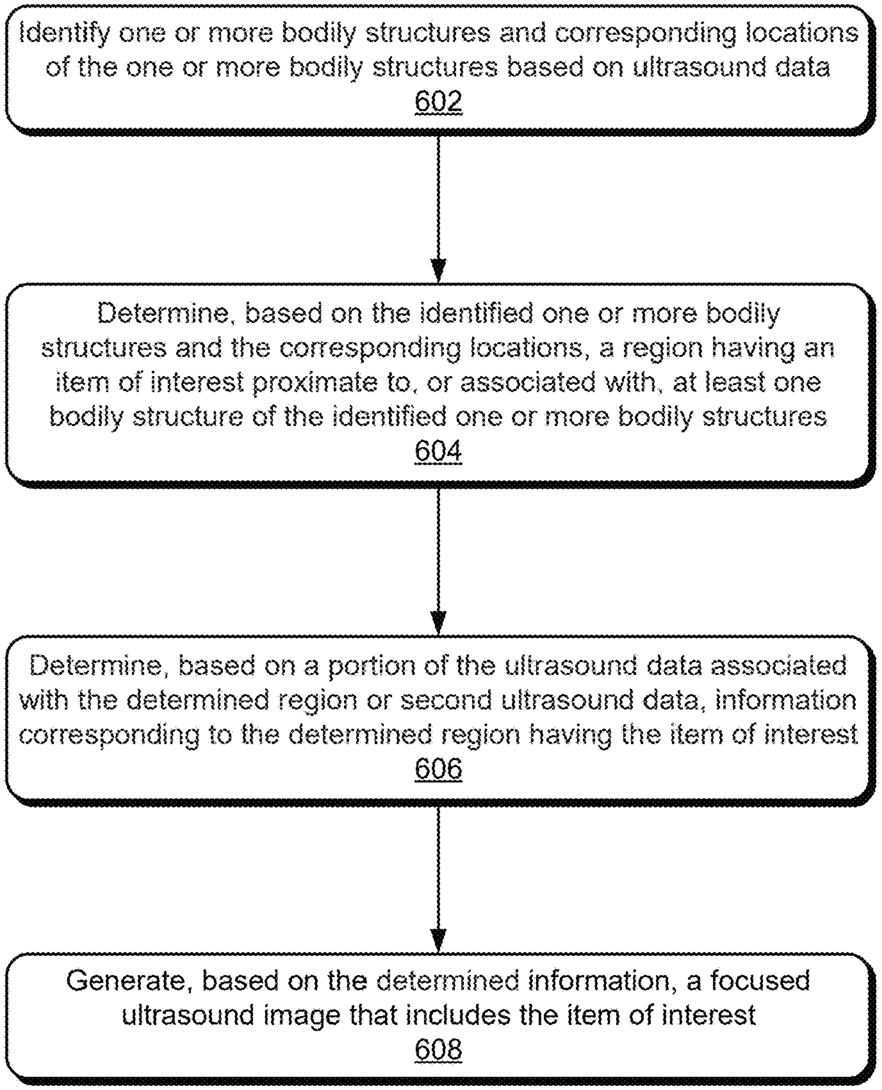
FIG. 6 depicts a method for an anatomy-directed ultrasound.

FIG. 6 depicts a method 600 for an anatomy-directed ultrasound. The method 600 is performed by the ultrasound system 100 described herein. At 602, an ultrasound system identifies one or more organs and corresponding locations of the one or more organs based on ultrasound data. For example, the ultrasound system 100 identifies which organs are represented in the ultrasound data 202 (e.g., organs shown in the ultrasound image 120) and their corresponding locations in the ultrasound data 202.

At 604, the ultrasound system determines, based on the identified one or more organs and the corresponding locations, a region having an item of interest proximate to, or associated with, at least one organ of the one or more identified organs. For example, the refinement module 114 of the ultrasound system 100 uses the identified organs and corresponding locations to identify a region (e.g., region of interest) that is likely to have the item of interest. The determination may be based on trained data indicating that a particular region proximate or adjacent to a particular organ has a tendency or likelihood (e.g., probability value greater than a threshold value) of having the item of interest.

At 606, the ultrasound system determines, based on a portion of ultrasound data associated with the region or second ultrasound data, information corresponding to the region having the item of interest. For example, the ultrasound system 100 uses a portion of the ultrasound data (e.g., the cropped image 212, the weight map 214) or second ultrasound data (e.g., the new ultrasound data 218 generated using the imaging parameters 216) to determine information such as a boundary enclosing the item of interest.

At 608, the ultrasound system generates, based on the information, a focused ultrasound image that includes the item of interest. For example, the ultrasound system 100 uses the information corresponding to the region having the item of interest to generate the segmentation image 220, which includes the item of interest (e.g., the segmentation 222).

In an example, the ultrasound data includes an ultrasound image of the reflections of the ultrasound signals. In another example, the ultrasound data includes data representing the ultrasound image. In yet another example, the determined region having the item of interest proximate to, or associated with, at least one bodily structure of the identified one or more bodily structures is determined based on a probability that is greater than a threshold value, where the probability is based on a collection of at least other ultrasound data.

In some implementations, the one or more modules are configured to provide the ultrasound data as input to a first machine-learned model and obtain an output from the first machine-learned model. Further, the one or more bodily structures and the corresponding locations of the one or more bodily structures in the ultrasound data may be identified based on the output from the first machine-learned model. In addition or alternative to such implementations, the first machine-learned model may include a neural network.

In some implementations, the one or more modules are further implemented to (i) provide the portion of the ultrasound data associated with the determined region or the second ultrasound data as input to a second machine-learned model and (ii) obtain an output from the second machine-learned model that includes segmentation data associated with the item of interest in the determined region. In addition or alternative to such implementations, the second machine-learned model may include a neural network stored at the ultrasound system.

In some implementations, the one or more modules of the ultrasound system are further implemented to scale the focused ultrasound data to align the item of interest with at least a portion of the ultrasound data generated by the ultrasound scanner.

In some implementations, the one or more modules are further implemented to classify the item of interest. In addition or alternative to such implementations, the item of interest may be identified as free fluid and the item of interest may be classified based on a classification selected from a group consisting of blood and non-blood fluids. In addition or alternative to such implementations, the item of interest may be identified as free fluid and the item of interest may be classified based on a classification selected from a group consisting of blood, extracellular fluid, and urine.

In some implementations, the one or more modules are further implemented to generate, based on the determined region, the portion of the ultrasound data associated with the determined region. In addition or alternative to such implementations, the portion of the ultrasound data associated with the determined region may also include a cropped ultrasound image or a weight map.

In some implementations, the one or more modules are further implemented to generate, based on the determined region, imaging parameters usable to refocus an ultrasound scan of the determined region. In addition or alternative to such implementations, the second ultrasound data may also be generated by an ultrasound machine according to the imaging parameters.

Figure 7:
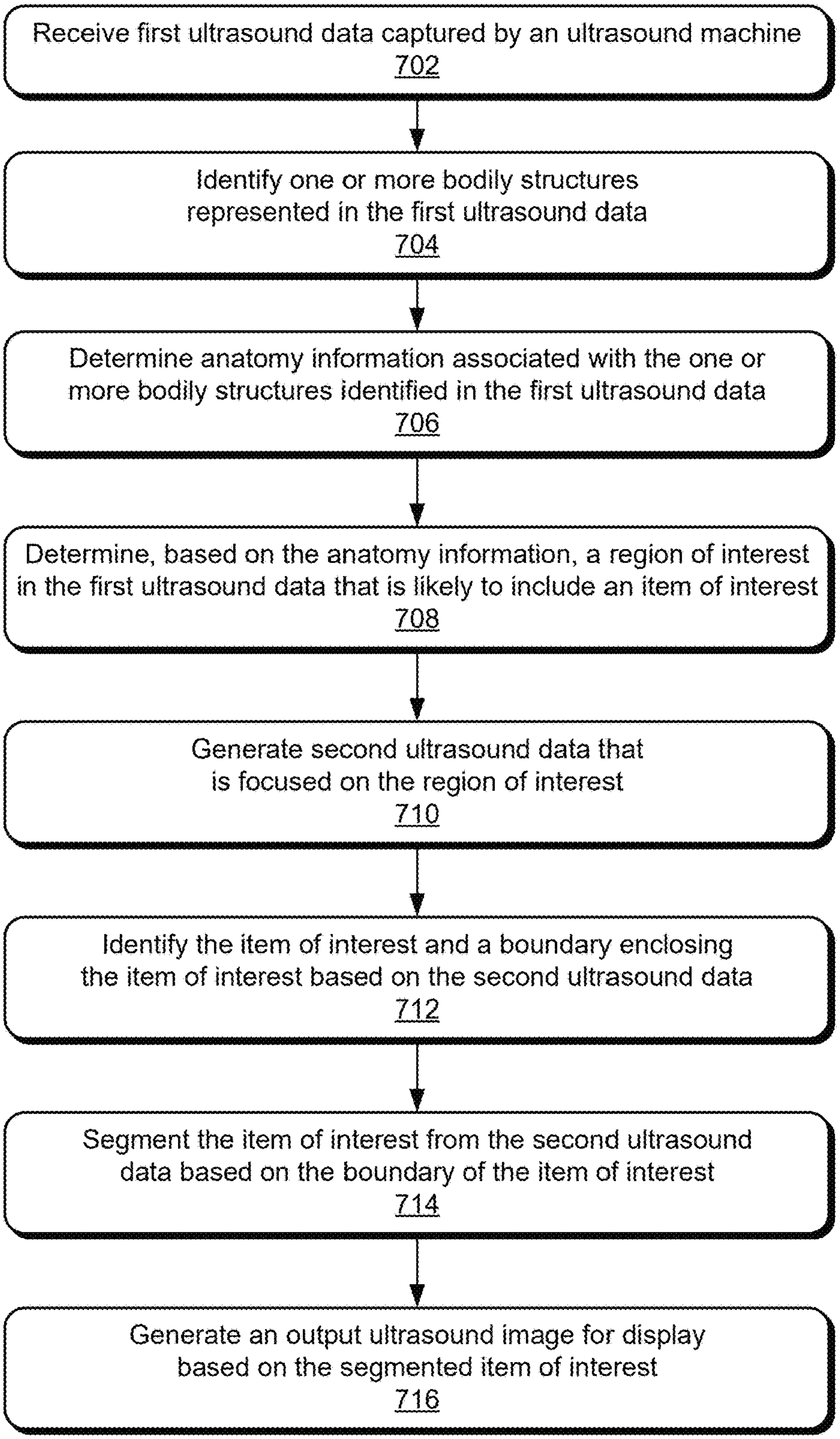
FIG. 7 depicts another method for an anatomy-directed ultrasound.

FIG. 7 depicts another method 700 for anatomy-directed ultrasound. The method 700 is performed by the ultrasound system 100 described herein. At 702, first ultrasound data captured by an ultrasound machine is received. For example, the ultrasound scanner 104 of the ultrasound machine 102 generates ultrasound data based on reflections of ultrasound signals transmitted by the ultrasound scanner 104 at an anatomy.

At 704, one or more organs represented in the first ultrasound data are identified. For example, the first ultrasound data can be fed as input to an ML model (e.g., the first ML model 112-1) and the output of the ML model can include identification of the one or more organs that are represented in the first ultrasound data.

At 706, anatomy information associated with the one or more organs identified in the first ultrasound data is determined. In implementations, the anatomy information includes organ type and location of each of the identified organs represented in the first ultrasound data. In some implementations, the anatomy information is included in the output of the first ML model (e.g., first ML model 112-1).

At 708, a region of interest in the first ultrasound data that is likely to include an item of interest is identified based on the anatomy information. In some implementations, the region of interest is determined by a refinement module (e.g., the refinement module 114) based on the anatomy information received from the first ML model 112-1. In one example, the refinement module is an ML model trained to identify regions of interest based on identified organs and tendencies (or likelihood) of accumulation or existence of particular items of interest.

At 710, second ultrasound data is generated that is focused on the region of interest. In one example, the second ultrasound data is a cropped version (e.g., the cropped image 212, subset) of the first ultrasound data. The cropped version may be centered on the region of interest. In another example, the second ultrasound data is a weight map (e.g., the weight map 214) that has weights indicating the one or more identified organs and/or the region of interest. In yet another example, the second ultrasound data is new or refocused ultrasound data (e.g., the new ultrasound data 218) generated by the ultrasound machine 102 based on new imaging parameters (e.g., the imaging parameters 216) generated or defined by the refinement module 114.

At 712, the item of interest and a boundary enclosing the item of interest are identified based on the second ultrasound data. In an example, the second ultrasound data is fed as input into another ML model (e.g., the second ML model 112-2), which is trained to identify items of interest in focused ultrasound data (e.g., the segmentation image 220, the segmentation 222). An output of the ML model identifies a boundary that encloses the item of interest (e.g., free fluid, lesion, implant). The boundary may be an elliptical (including circular) shape, an oblong shape, or another shape that generally encloses the item of interest. In some examples, the boundary can follow the contour (e.g., actual boundary) of the item of interest in the second ultrasound data.

At 714, the item of interest is segmented from the second ultrasound data based on the boundary of the item of interest. In an example, the item of interest is segmented from the second ultrasound data by the same ML model (e.g., the second ML model 112-2) that identified the boundary. In yet another example, a different ML model segments the item of interest from the second ultrasound data. The ML model segments, extracts, or removes the item of interest from the second ultrasound data by using the boundary. For instance, the ML model can extract a portion of the second ultrasound data that is inside the boundary. In another example, the ML model suppresses at least a portion of the second ultrasound data that is outside the boundary of the item of interest.

At 716, an output ultrasound image for display is generated based on the segmented item of interest. For example, the ultrasound system 100 generates an ultrasound image for display via the display device 108 to enable the ultrasound operator to view a representation of the item of interest. The displayed ultrasound image can include the segmentation image 220.

In an example, generating the second ultrasound data that is focused on the determined region of interest is based on (i) suppressing at least a portion of the first ultrasound data that is outside of the determined region of interest and (ii) removing at least a portion of the first ultrasound data that is outside of the determined region of interest.

In some implementations, segmenting the item of interest from the second ultrasound data includes suppressing at least a portion of the second ultrasound data outside the boundary. In addition or alternative to such implementations, segmenting the item of interest from the second ultrasound data may include extracting a portion of the second ultrasound data that is inside the boundary. In addition or alternative to such implementations, generating the output image may include generating a displayable image having the extracted portion of the second ultrasound data that is inside the boundary.

In some implementations, the method further comprises receiving a user selection of a visual parameter of the output image and displaying the output image with the segmentation of the item of interest configured according to the user-selected visual parameter.

In some implementations, the one or more bodily structures include two bodily structures and the method further comprises: determining, based on a respective location of each of the two bodily structures, a distance between the two bodily structures; determining whether the distance between the two bodily structures is greater than a threshold distance; and determining that the item of interest is free fluid based on a determination that the distance is greater than the threshold distance.

In some implementations, generating the second ultrasound data includes at least one of: cropping the first ultrasound data to generate the second ultrasound data, uncropped ultrasound data being the first ultrasound data, the second ultrasound data focusing on the determined region of interest; generating a weight map indicating the determined region of interest in the second ultrasound data; and generating refocused ultrasound data based on additional reflections of additional ultrasound signals transmitted by the ultrasound scanner to at least a portion of the anatomy in accordance with imaging parameters generated based on the determined region of interest in the first ultrasound data.

Example Models and Devices

As described, many of the features described herein can be implemented using a machine-learned model. For the purposes of this disclosure, a machine-learned model is any model that accepts an input, analyzes, and/or processes the input based on an algorithm derived via machine-learning training, and provides an output. A machine-learned model can be conceptualized as a mathematical function of the following form:

$$f(\hat{s}, \theta) = \hat{y} \qquad \text{Equation (1)}$$

In Equation (1), the operator f represents the processing of the machine-learned model based on an input and providing an output. The term $\hat{s}$ represents a model input, such as ultrasound data. The model analyzes/processes the input $\hat{s}$ using parameters $\theta$ to generate output $\hat{y}$ (e.g., the anatomy information 210 or the segmentation image 220). Both $\hat{s}$ and $\hat{y}$ can be scalar values, matrices, vectors, or mathematical representations of phenomena such as categories, classifications, image characteristics, the images themselves, text, labels, or the like. The parameters $\theta$ can be any suitable mathematical operations, including but not limited to applications of weights and biases, filter coefficients, summations or other aggregations of data inputs, distribution parameters such as mean and variance in a Gaussian distribution, linear-algebra-based operators, or other parameters, including combinations of different parameters, suitable to map data to the desired output.

Figure 8:
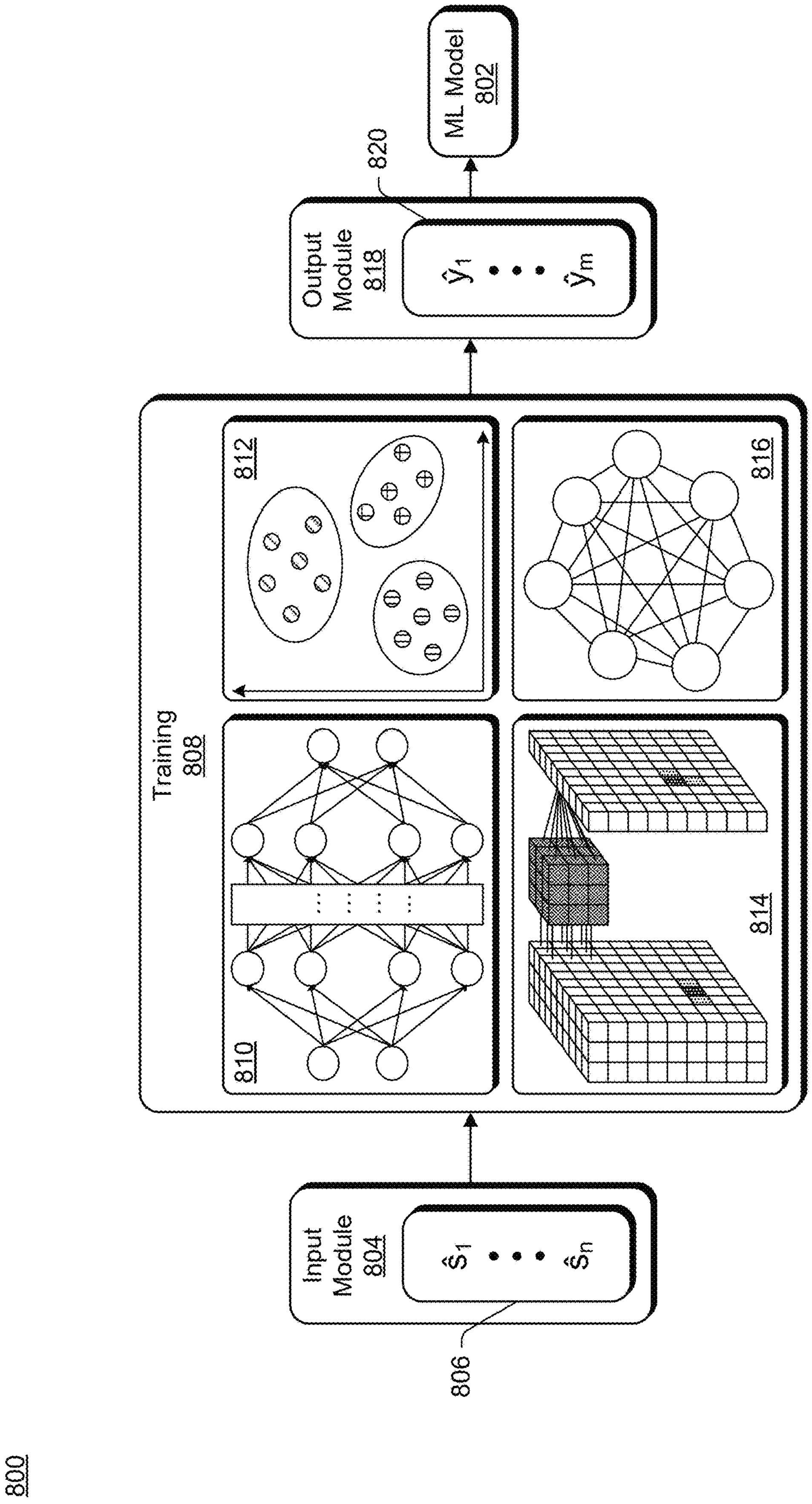
FIG. 8 represents an example machine-learning architecture used to train a machine-learned model.

FIG. 8 represents an example machine-learning architecture 800 used to train a machine-learned model M 802 (e.g., ML model 112). An input module 804 accepts an input $\hat{s}$ 806, which can be an array with members $\hat{s}_1$ through $\hat{s}_n$. The input $\hat{s}$ 806 is fed into a training module 808, which processes the input s 806 based on the machine-learning architecture 800. For example, if the machine-learning architecture 800 uses a multilayer perceptron (MLP) model 810, the training module 808 applies weights and biases to the input $806 through one or more layers of perceptrons, each perceptron performing a fit using its own weights and biases according to its given functional form. MLP weights and biases can be adjusted so that they are optimized against a least mean square, logcosh, or other optimization function (e.g., loss function) known in the art. Although an MLP model 810 is described here as an example, any suitable machine-learning technique can be employed, some examples of which include but are not limited to k-means clustering 812, convolutional neural networks (CNN) 814, a Boltzmann machine 816, Gaussian mixture models (GMM), and long short-term memory (LSTM). The training module 808 provides an input to an output module 818. The output module 818 analyzes the input from the training module 808 and provides a prediction output in the form of $\hat{y}$ 820, which can be an array with members $\hat{y}_1$ through $\hat{y}_m$. The prediction output 820 can represent a known correlation with the input $\hat{s}$ 806, such as, for example, the anatomy information 210, the segmentation 222 of the item of interest, or the segmentation image 220.

In some examples, the input $\hat{s}$ 806 can be training input labeled with known output correlation values, and these known values can be used to optimize the output $\hat{y}$ 820 in training against the optimization/loss function. In other examples, the machine-learning architecture 800 can categorize the output $\hat{y}$ 820 values without being given known correlation values to the inputs $\hat{s}$ 806. In some examples, the machine-learning architecture 800 can be a combination of machine-learning architectures. By way of example, a first network can use input $\hat{s}$ 806 and provide prediction output $\hat{y}$ 820 as an input $\hat{s}_{ML}$ to a second machine-learned architecture, with the second machine-learning architecture providing a final prediction output $\hat{y}_f$. In another example, one or more machine-learning architectures can be implemented at various points throughout the training module 808.

In some ML models, all layers of the model are fully connected. For example, all perceptrons in an MLP model act on every member of $\hat{s}$. For an MLP model with a 100×100 pixel image as the input, each perceptron provides weights/biases for 10,000 inputs. With a large, densely layered model, this may result in slower processing and/or issues with vanishing and/or exploding gradients. A CNN, which may not be a fully connected model, can process the same image using 5×5 tiled regions, requiring only 25 perceptrons with shared weights, giving much greater efficiency than the fully connected MLP model.

Figure 9:
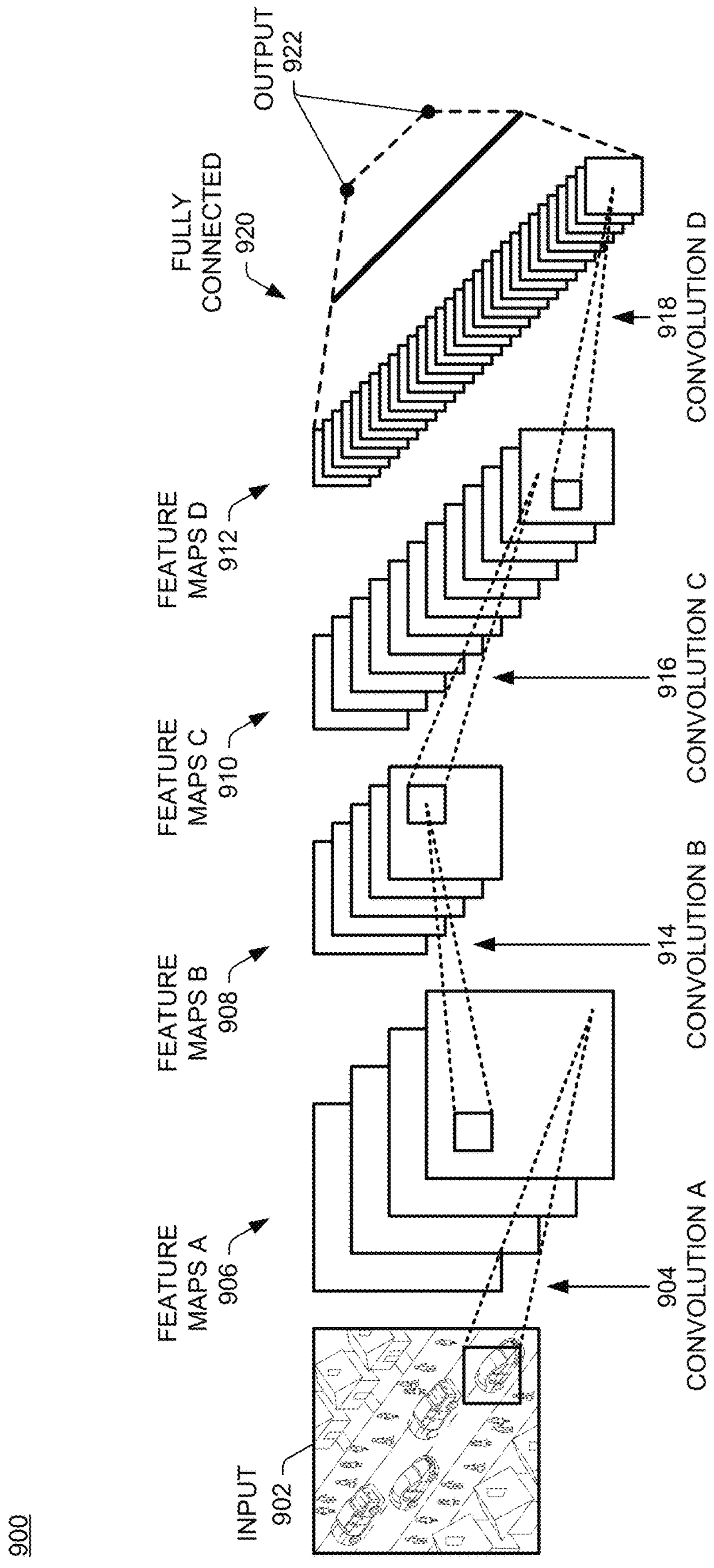
FIG. 9 represents an example model using a convolutional neural network (CNN) to process input image, which includes representations of objects that may be identified via object recognition.

FIG. 9 represents an example model 900 using a CNN to process input image 902, which includes representations of objects that may be identified via object recognition, such as people or cars. Although this example includes people and cars as general objects in the input image 902, the input image 902 can include the ultrasound image 120, as described above, having representations of anatomy, such as bodily structures. Convolution A 904 may be performed to create a first set of feature maps (e.g., feature maps A 906). A feature map may be a mapping of aspects of the input image 902 given by a filter element of the CNN. This process may be repeated using feature maps A 906 to generate further feature maps B 908, feature maps C 910, and feature maps D 912 using convolution B 914, convolution C 916, and convolution D 918, respectively. In this example, feature maps D 912 become the input for fully connected network layers 920. In this way, the ML model can be trained to recognize certain elements of the image, such as people or cars, and provide an output 922 that, for example, identifies the recognized elements.

Although the example of FIG. 9 shows a CNN as a part of a fully connected network, other architectures are possible and this example should not be seen as limiting. There may be more or fewer layers in the CNN. A CNN component for a model may be placed in a different order, or the model may contain additional components or models. There may be no fully connected components, such as a fully convolutional network. Additional aspects of the CNN, such as pooling, downsampling, upsampling, or other aspects known to people skilled in the art may also be employed.

Figure 10:
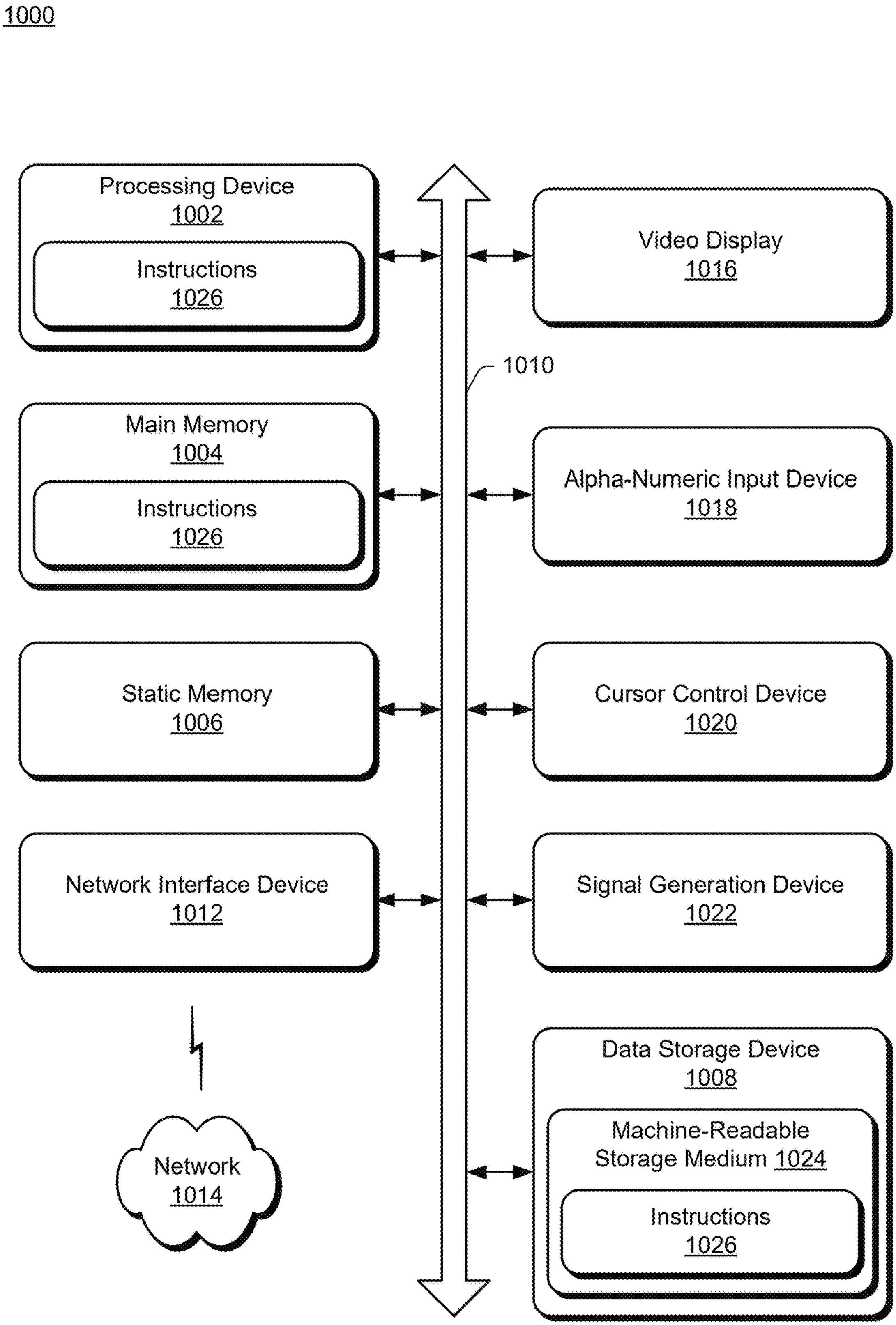
FIG. 10 illustrates a block diagram of an example computing device that can perform one or more of the operations described herein, in accordance with some implementations.

FIG. 10 illustrates a block diagram of an example computing device 1000 that can perform one or more of the operations described herein, in accordance with some implementations. The computing device 1000 can be connected to other computing devices in a LAN, an intranet, an extranet, and/or the Internet. The computing device can operate in the capacity of a server machine in a client-server network environment or in the capacity of a client in a peer-to-peer network environment. The computing device can be provided by a personal computer (PC), a server computer, a desktop computer, a laptop computer, a tablet computer, a smartphone, or any machine capable of executing a set of instructions (sequential or otherwise) that specify actions to be taken by that machine. Further, while only a single computing device is illustrated, the term "computing device" shall also be taken to include any collection of computing devices that individually or jointly execute a set (or multiple sets) of instructions to perform the methods discussed herein. In some implementations, the computing device 1000 is one or more of an ultrasound machine, an access point, and a packet-forwarding component.

The example computing device 1000 can include a processing device 1002 (e.g., a general-purpose processor, a PLD, etc.), a main memory 1004 (e.g., synchronous dynamic random-access memory (DRAM), read-only memory (ROM)), and a static memory 1006 (e.g., flash memory and a data storage device 1008), which can communicate with each other via a bus 1010. The processing device 1002 can be provided by one or more general-purpose processing devices such as a microprocessor, a central processing unit, or the like. In an illustrative example, the processing device 1002 comprises a complex instruction set computing (CISC) microprocessor, a reduced instruction set computing (RISC) microprocessor, a very long instruction word (VLIW) microprocessor, or a processor implementing other instruction sets or processors implementing a combination of instruction sets. The processing device 1002 can also comprise one or more special-purpose processing devices such as an application-specific integrated circuit (ASIC), a field programmable gate array (FPGA), a digital signal processor (DSP), a network processor, or the like. The processing device 1002 can be configured to execute the operations described herein, in accordance with one or more aspects of the present disclosure, for performing the operations and steps discussed herein.

The computing device 1000 can further include a network interface device 1012, which can communicate with a network 1014. The computing device 1000 also can include a video display unit 1016 (e.g., a liquid crystal display (LCD), organic light-emitting diode (OLED), or a cathode ray tube (CRT)), an alphanumeric input device 1018 (e.g., a keyboard), a cursor control device 1020 (e.g., a mouse), and an acoustic signal generation device 1022 (e.g., a speaker and/or a microphone). In one embodiment, the video display unit 1016, the alphanumeric input device 1018, and the cursor control device 1020 can be combined into a single component or device (e.g., an LCD touch screen).

The data storage device 1008 can include a computer-readable storage medium 1024 on which can be stored one or more sets of instructions 1026 (e.g., instructions for carrying out the operations described herein, in accordance with one or more aspects of the present disclosure). The instructions 1026 can also reside, completely or at least partially, within the main memory 1004 and/or within the processing device 1002 during execution thereof by the computing device 1000, where the main memory 1004 and the processing device 1002 also constitute computer-readable media. The instructions can further be transmitted or received over the network 1014 via the network interface device 1012.

Various techniques are described in the general context of software, hardware elements, or program modules. Generally, such modules include routines, programs, objects, elements, components, data structures, and so forth that perform particular tasks or implement particular abstract data types. The terms "module," "functionality," and "component" as used herein generally represent software, firmware, hardware, or a combination thereof. In some aspects, the modules described herein (e.g., the refinement module 114, the pre-process module, the imaging module 502, the cropping module 504, the mapping module 506, the input module 804, the training module 808, and the output module 818) are embodied in the data storage device 1008 of the computing device 1000 as executable instructions or code. Although represented as software implementations, the described modules can be implemented as any form of a control application, software application, signal-processing and control module, hardware, or firmware installed on the computing device 1000.

While the computer-readable storage medium 1024 is shown in an illustrative example to be a single medium, the term "computer-readable storage medium" should be taken to include a single medium or multiple media (e.g., a centralized or distributed database and/or associated caches and servers) that store the one or more sets of instructions. The term "computer-readable storage medium" shall also be taken to include any medium that is capable of storing, encoding, or carrying a set of instructions for execution by the machine and that causes the machine to perform the methods described herein. The term "computer-readable storage medium" shall accordingly be taken to include, but not be limited to, solid-state memories, optical media, and magnetic media.

Conclusion

Embodiments of anatomy-directed ultrasound as described herein are advantageous, as they can enhance performance of a segmentation, providing augmented information with increased accuracy and fewer false positives to help with diagnosis and thereby improve care provided to a patient. The anatomy-directed ultrasound can also reduce manual, explicit configuration (e.g., setting imaging parameters) of the ultrasound system by an operator compared to conventional ultrasound systems. The operator may reduce diversions from a patient and towards the ultrasound system, further resulting in an improvement to a patient's care.

What is claimed is:

1. An ultrasound system comprising:

an ultrasound scanner configured to generate ultrasound data based on reflections of ultrasound signals transmitted by the ultrasound scanner at an anatomy;

a memory;

one or more computer processors configured to execute instructions stored in the memory;

a first machine-learned (ML) model stored in the memory, the first ML model configured to identify one or more bodily structures and corresponding locations of the one or more bodily structures;

a refinement module stored in the memory, the refinement module configured to generate a weight map corresponding to the ultrasound data, the weight map including numerical values that each represent an area of the ultrasound data and a likelihood that the area includes an item of interest, the weight map indicating at least one region of the ultrasound data that is proximate to, or associated with, at least one bodily structure of the one or more bodily structures and that has a likelihood greater than a threshold value of including the item of interest; and a second ML model stored in the memory, the second ML model configured to:

perform a focused search, based on the weight map, for the item of interest in the at least one region of the ultrasound data;

determine, based on the focused search, information corresponding to the at least one region; and generate, based on the information, focused ultrasound data that includes a segmentation of the item of interest.

2. The ultrasound system of claim 1, wherein:

the ultrasound data includes an ultrasound image of the reflections of the ultrasound signals; or the ultrasound data includes data representing the ultrasound image.

3. The ultrasound system of claim 1, wherein the likelihood of the at least one region including the item of interest is based on a probability, the probability based on a collection of at least other ultrasound data.

4. The ultrasound system of claim 1, wherein the likelihood of the at least one region including the item of interest is based on a statistical value.

5. The ultrasound system of claim 1, wherein one or more of the first ML model and the second ML model includes a neural network.

6. The ultrasound system of claim 1, wherein the numerical values include:

high-numerical values representing first areas of the ultrasound data that have a high probability of including the item of interest, the high probability being greater than the threshold value, the high-numerical values corresponding to low-intensity reflections of the ultrasound signals in proximity to the one or more bodily structures; and low-numerical values representing second areas of the ultrasound data that have a low probability of including the item of interest, the low probability being below the threshold value, the low-numerical values corresponding to high-intensity reflections of the ultrasound signals in proximity to the one or more bodily structures.

7. The ultrasound system of claim 1, wherein the numerical values include non-binary values in a range of values representing various levels of interest in the ultrasound data.

8. The ultrasound system of claim 1, wherein the one or more computer processors is configured to execute the instructions stored in the memory to classify the item of interest.

9. The ultrasound system of claim 8, wherein:

the item of interest is identified as free fluid; and the item of interest is classified as one of blood and a non-blood fluid.

10. The ultrasound system of claim 8, wherein:

the item of interest is identified as free fluid; and the item of interest is classified as one of blood, extracellular fluid, and urine.

11. The ultrasound system of claim 1, wherein the one or more computer processors is configured to execute the instructions stored in the memory to:

identify the item of interest as free fluid; and classify a type of the free fluid based on one or more of a location of the free fluid relative to one or more organs, an elasticity of the free fluid, a pattern in the focused ultrasound data, a frequency of the ultrasound signals, and organ locations.

12. The ultrasound system of claim 1, wherein the information corresponding to the at least one region includes a boundary enclosing the item of interest.

13. A method for anatomy-directed ultrasound, the method comprising:

receiving ultrasound data generated by an ultrasound scanner based on reflections of ultrasound signals transmitted by the ultrasound scanner at an anatomy;

identifying one or more bodily structures and corresponding locations of the one or more bodily structures in the ultrasound data;

generating a weight map corresponding to the ultrasound data, the weight map including numerical values that each represent an area of the ultrasound data and a likelihood that the area includes an item of interest, the weight map indicating at least one region of the ultrasound data that is proximate to, or associated with, at least one bodily structure of the one or more bodily structures and that has a likelihood greater than a threshold value of including the item of interest;

performing a focused search, based on the weight map, for the item of interest in the at least one region of the ultrasound data;

determining, based on the focused search, information corresponding to the at least one region; and generating, based on the information, focused ultrasound data that includes a segmentation of the item of interest.

14. The method of claim 13, wherein the likelihood of the at least one region including the item of interest is based on a probability, the probability based on a collection of at least other ultrasound data.

15. The method of claim 13, wherein the likelihood of the at least one region including the item of interest is based on a statistical value.

16. The method of claim 13, wherein the numerical values include:

high-numerical values representing first areas of the ultrasound data that have a high probability of including the item of interest, the high probability being greater than the threshold value, the high-numerical values corresponding to low-intensity reflections of the ultrasound signals in proximity to the one or more bodily structures; and low-numerical values representing second areas of the ultrasound data that have a low probability of including the item of interest, the low probability being below the threshold value, the low-numerical values corresponding to high-intensity reflections of the ultrasound signals in proximity to the one or more bodily structures.

17. The method of claim 13, wherein the numerical values include non-binary values in a range of values representing various levels of interest in the ultrasound data.

18. The method of claim 13, further comprising:

identifying the item of interest as free fluid; and classifying the item of interest as one of blood and a non-blood fluid.

19. The method of claim 13, further comprising:

identifying the item of interest as free fluid; and classifying the item of interest as one of blood, extracellular fluid, and urine.

20. The method of claim 13, further comprising:

identifying the item of interest as free fluid; and classifying a type of the free fluid based on one or more of a location of the free fluid relative to one or more organs, an elasticity of the free fluid, a pattern in the focused ultrasound data, a frequency of the ultrasound signals, and organ locations.

* * * * *